United States Patent
Koyama (10) Patent No.: US 8,616,413 B2
(45) Date of Patent: Dec. 31, 2013

(54) SYRINGE

(75) Inventor: Shingo Koyama, Yamanashi-ken (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 0 days.

(21) Appl. No.: 13/395,983

(22) PCT Filed: Mar. 2, 2011

(86) PCT No.: PCT/JP2011/054722
§ 371 (c)(1),
(2), (4) Date: Mar. 14, 2012

(87) PCT Pub. No.: WO2011/108574
PCT Pub. Date: Sep. 9, 2011

(65) Prior Publication Data
US 2012/0168464 A1 Jul. 5, 2012

(30) Foreign Application Priority Data
Mar. 3, 2010 (JP) .................................. 2010-047032

(51) Int. Cl.
B67B 1/00 (2006.01)
B65D 47/10 (2006.01)
A61M 5/00 (2006.01)

(52) U.S. Cl.
USPC .............. 222/153.06; 222/541.6; 222/153.05; 604/111

(58) Field of Classification Search
USPC ......... 222/137, 145.5, 153.05, 153.06, 541.6, 222/541.1; 215/47, 48; 604/110, 111
See application file for complete search history.

(56) References Cited

U.S. PATENT DOCUMENTS 4,176,755 A * 12/1979 Winchell .......................... 215/48
4,667,837 A * 5/1987 Vitello et al. .................. 215/228
(Continued)

FOREIGN PATENT DOCUMENTS

JP 8-308926 A 11/1996
JP 2002-315827 A 10/2002
(Continued)

OTHER PUBLICATIONS

International Search Report (PCT/ISA/210) issued on May 31, 2011, by Japanese Patent Office as the International Searching Authority for International Application No. PCT/JP2011/054722.

(Continued)

*Primary Examiner* — Paul R Durand
*Assistant Examiner* — Benjamin R Shaw
(74) *Attorney, Agent, or Firm* — Buchanan Ingersoll & Rooney PC (57) ABSTRACT

A syringe includes a syringe outer tube having a spout and a spout-mounted cap. The cap has a cap main body sealing the spout in a liquid-tight manner, a mounting section mounted onto the spout, and a breakable breaking section linking the cap main body and the mounting section to release the link upon breaking. The inner circumferential portion of the mounting section includes protrusions inserted into a groove on the outer circumferential portion of the spout which also has a tilted section tilted relative to the axis of the spout outer circumferential portion. When the cap is rotated along the axial direction of the syringe outer tube, the protrusions move along the tilted section of the groove. The mounting section is thus displaced in the base end direction and the braking section is pulled in the direction and breaks to separate the cap main body from the mounting section.

10 Claims, 6 Drawing Sheets

(56) References Cited

U.S. PATENT DOCUMENTS

| | | | |
|---|---|---|---|
| 6,190,364 B1 * | 2/2001 | Imbert | 604/256 |
| 6,491,665 B1 * | 12/2002 | Vetter et al. | 604/181 |
| 6,520,935 B1 | 2/2003 | Jansen et al. | |
| 6,524,278 B1 * | 2/2003 | Campbell et al. | 604/192 |
| 7,041,087 B2 * | 5/2006 | Henderson et al. | 604/200 |
| 7,648,481 B2 * | 1/2010 | Geiger et al. | 604/110 |
| 2004/0116858 A1 * | 6/2004 | Heinz et al. | 604/111 |
| 2008/0312602 A1 * | 12/2008 | Barrow-Williams et al. | 604/192 |
| 2011/0178475 A1 | 7/2011 | Tanaka et al. | |

FOREIGN PATENT DOCUMENTS

| | | |
|---|---|---|
| JP | 2004-26309 A | 1/2004 |
| JP | 2005-67701 A | 3/2005 |
| WO | WO 2007/015469 A1 | 2/2007 |

OTHER PUBLICATIONS

Written Opinion (PCT/ISA/237) issued on May 31, 2011, by Japanese Patent Office as the International Searching Authority for International Application No. PCT/JP2011/054722.

Chinese Office Action issued Sep. 23, 2013 by the Chinese Patent Office in corresponding Chinese Application No. 201180003689.8 and partial English translation thereof (6 pgs).

\* cited by examiner

SYRINGE

TECHNICAL FIELD

The present invention relates to a syringe.

BACKGROUND ART

There has been known a prefilled syringe in which a sterilized syringe outer tube is filled with a liquid product in an aseptic manner (see, for example, Patent Document 1). The prefilled syringe includes: the syringe outer tube having a spout through which the liquid product is ejected and a lock adapter rotatably supported on the spout; and a cap mounted onto the spout of the syringe outer tube and locked by a lock member. When the prefilled syringe described in Patent Document 1 is, in its unused state or in its unopened sealed state, the cap and the lock adapter are collectively covered with a film with a perforation in a state in which the cap is mounted on the syringe outer tube.

When the prefilled syringe in the unused state is unsealed and the cap is detached but the cap is then remounted, i.e., the prefilled syringe is recapped, without using the prefilled syringe, it is impossible to recognize at first glance that the prefilled syringe is in an already unsealed state. When the cap of a prefilled syringe is once opened, it is difficult to maintain the aseptic state inside the prefilled syringe for a long time, and, therefore, the liquid product needs to be used swiftly. If recapping is done as above-mentioned, however, there has been a problem that the recapped prefilled syringe which is low in asepticity may be put to use, while erroneously deeming it as in the unused state.

Patent Document 1: Japanese Laid-Open Patent Publication No. 2002-315827

SUMMARY OF INVENTION

It is an object of the present invention to provide a syringe which is excellent in tamperproofness.

In order to attain the above object, the present invention provides a syringe including:

a syringe outer tube having a tubular shape to be filled with a liquid and provided with a spout through which the liquid passes at a distal end portion thereof;

and a cap mounted to the spout, wherein the cap includes a cap main body which seals the spout in a liquid-tight manner, a ring-shaped mounting section which is disposed on a proximal end side of the cap main body and is mounted onto an outer circumferential portion of the spout, and a breaking section which links the cap main body and the mounting section and a link is releasable by breaking, one of an inner circumferential portion of the mounting section and the outer circumferential portion of the spout is formed with at least one projection, while the other is formed with a groove into which the projection is inserted and which has an inclined section that is inclined in relation to an axis of the other, and when the cap is rotated relative to the syringe outer tube around an axis of the syringe outer tube, the projection moves along the inclined section of the groove, whereby the mounting section is displaced in a proximal direction, and the breaking section is pulled in the same direction to break, thereby separating the cap main body from the mounting section so that the cap main body thus separated from the mounting section cannot be mounted again onto the spout.

In addition, in the syringe of the present invention, preferably, the projection is disposed at the inner circumferential portion of the mounting section, and the groove is disposed at the outer circumferential portion of the spout.

Further, in the syringe of the present invention, preferably, the spout includes a reduced diameter section having a reduced outside diameter, and a ring-shaped lock adapter which is concentrically disposed at an outer circumferential portion of the reduced diameter section and which locks a mating member connected to the reduced diameter section, with the groove being disposed at an outer circumferential portion of the lock adapter.

In addition, in the syringe of the present invention, preferably, a plurality of the projections are disposed, and the groove is disposed correspondingly to each of the projections respectively.

Further, the syringe of the present invention, preferably, is so constituted that the operating direction of the rotating operation is restricted.

In addition, in the syringe of the present invention, preferably, the lock adapter is formed with a female screw which comes into screw engagement with the mating member at an inner circumferential portion thereof, and the female screw protrudes when the cap main body is separated.

Further, in the syringe of the present invention, preferably, the groove is formed in a part of the circumferential direction of the other.

In addition, in the syringe of the present invention, preferably, the breaking section is made up of a plurality of thin portions disposed intermittently around the axis of the mounting section.

Further, in the syringe of the present invention, preferably, the part of the cap main body which abuts against the spout to seal the spout is constituted by an elastic body, and the cap main body is biased toward the distal direction by an elastic force of the elastic body.

In addition, in the syringe of the present invention, preferably, the cap main body has a grip section which has a flat shape and which is gripped when the rotating operation is conducted.

DESCRIPTION OF EMBODIMENTS

Now, a syringe according to the present invention will be described in detail below, based on a preferred embodiment shown in the accompanying drawings.

Figure 1:
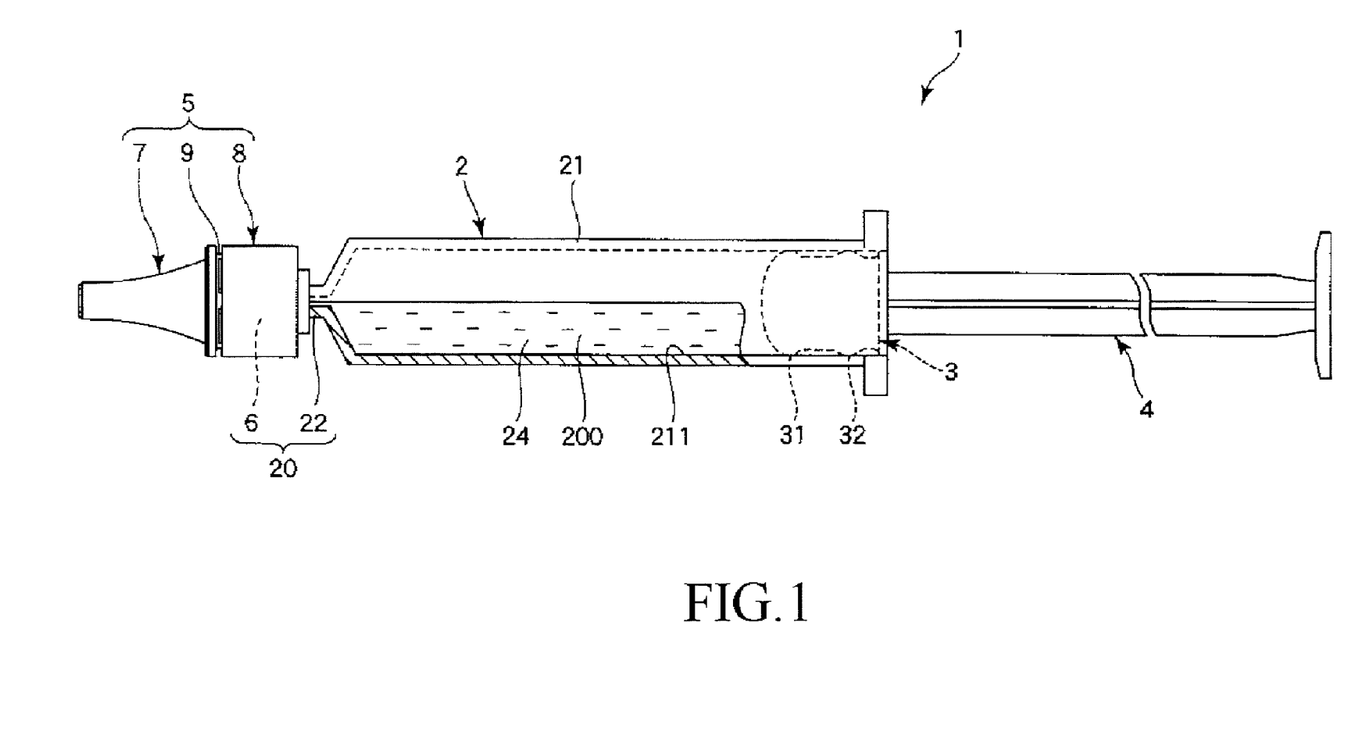
FIG. 1 is a side view showing an embodiment of a syringe according to the present invention.
Figure 2:
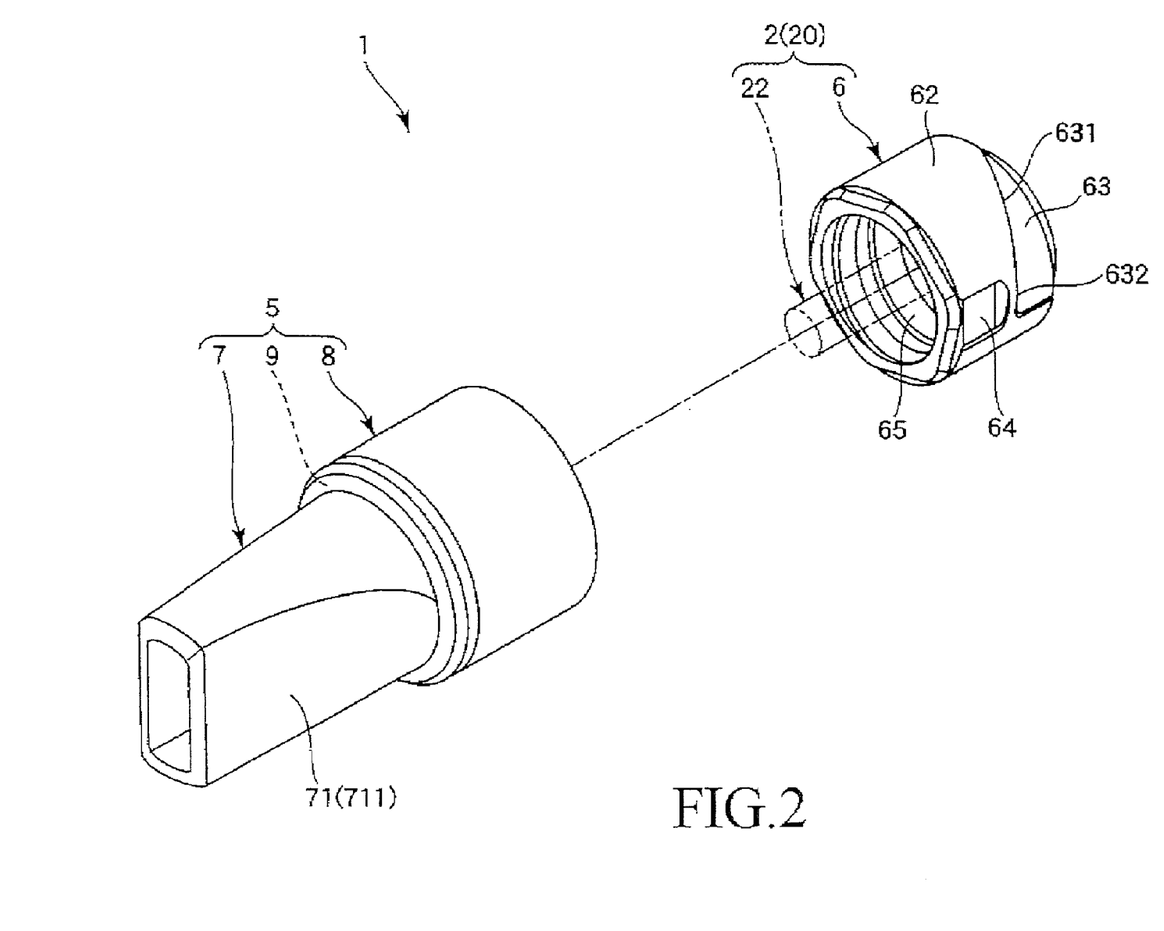
FIG. 2 is an exploded perspective view of a distal-side part of the syringe shown in FIG. 1.
Figure 3:
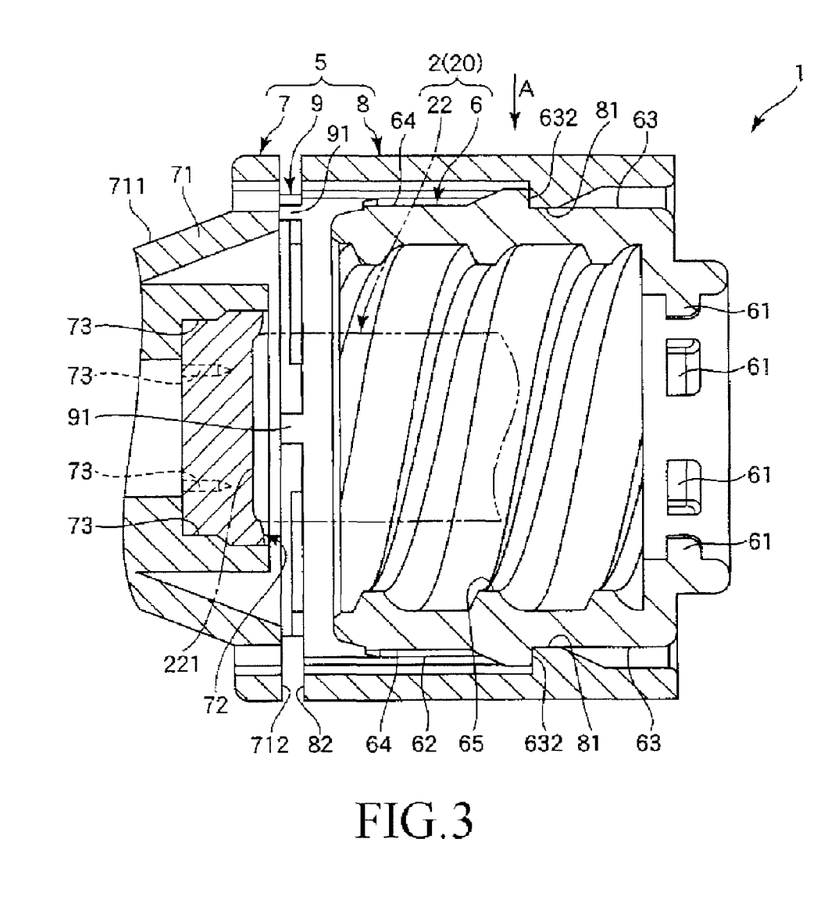
FIG. 3 is a longitudinal sectional view for sequentially showing the process of an unsealing (seal-breaking) operation of the syringe shown in FIG. 1.
Figure 4:
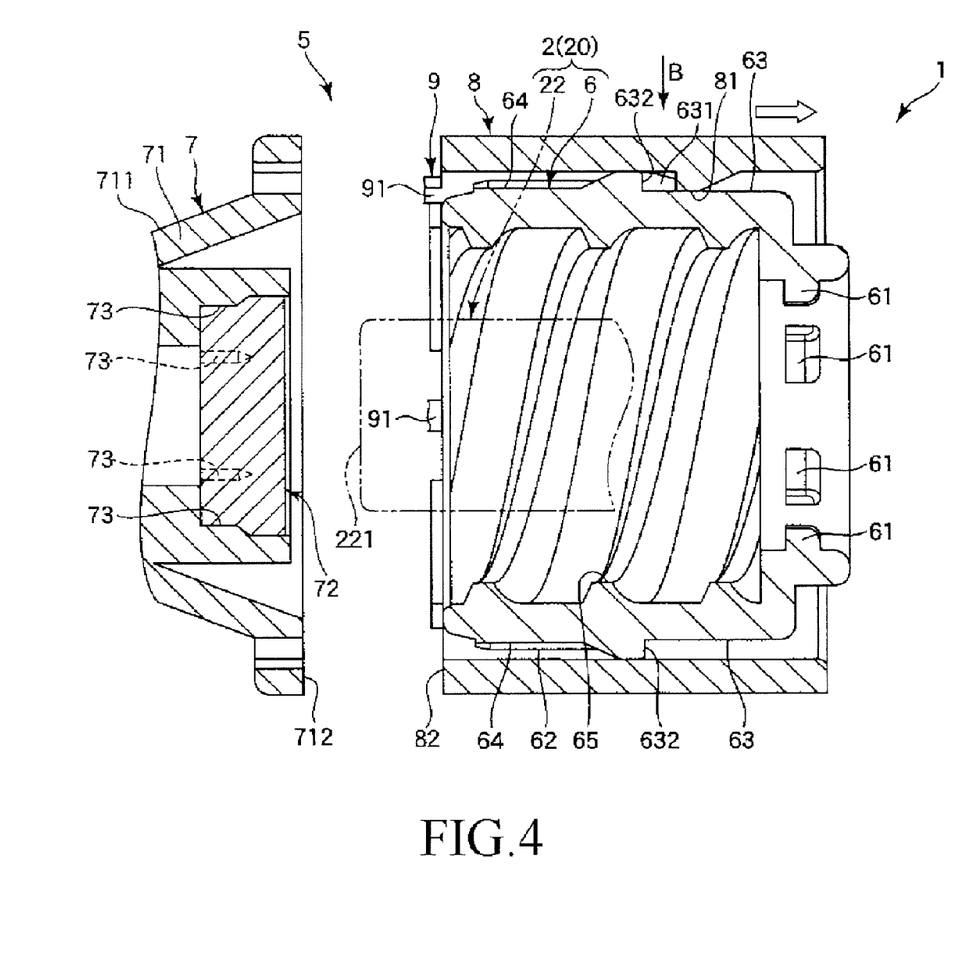
FIG. 4 is a longitudinal sectional view for sequentially showing the process of the unsealing operation of the syringe shown in FIG. 1.
Figure 5:
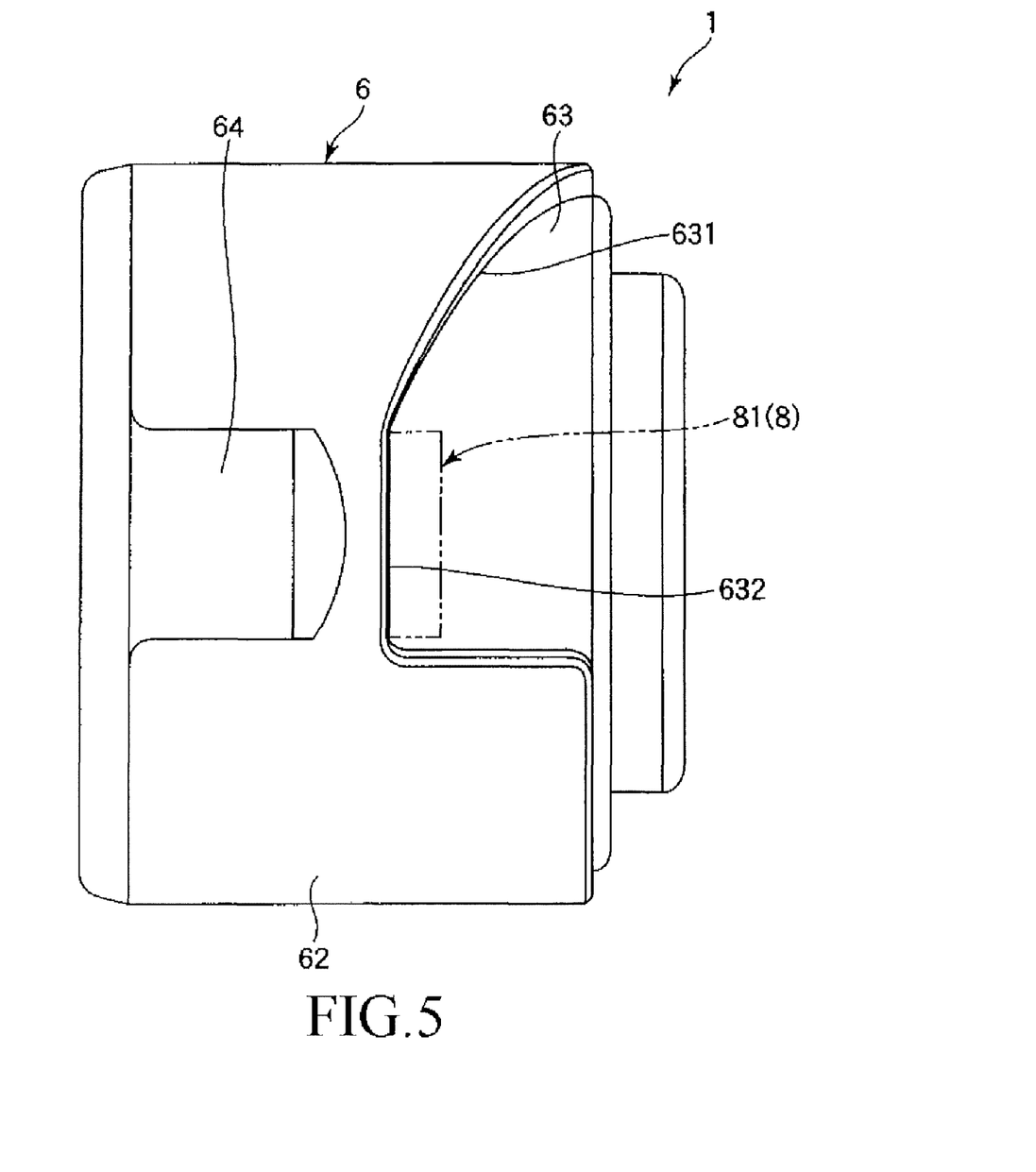
FIG. 5 is a view showing the positional relationship between a lock adapter of a syringe outer tube and a mounting section of a cap, as viewed from the direction of arrow A in FIG. 3.
Figure 6:
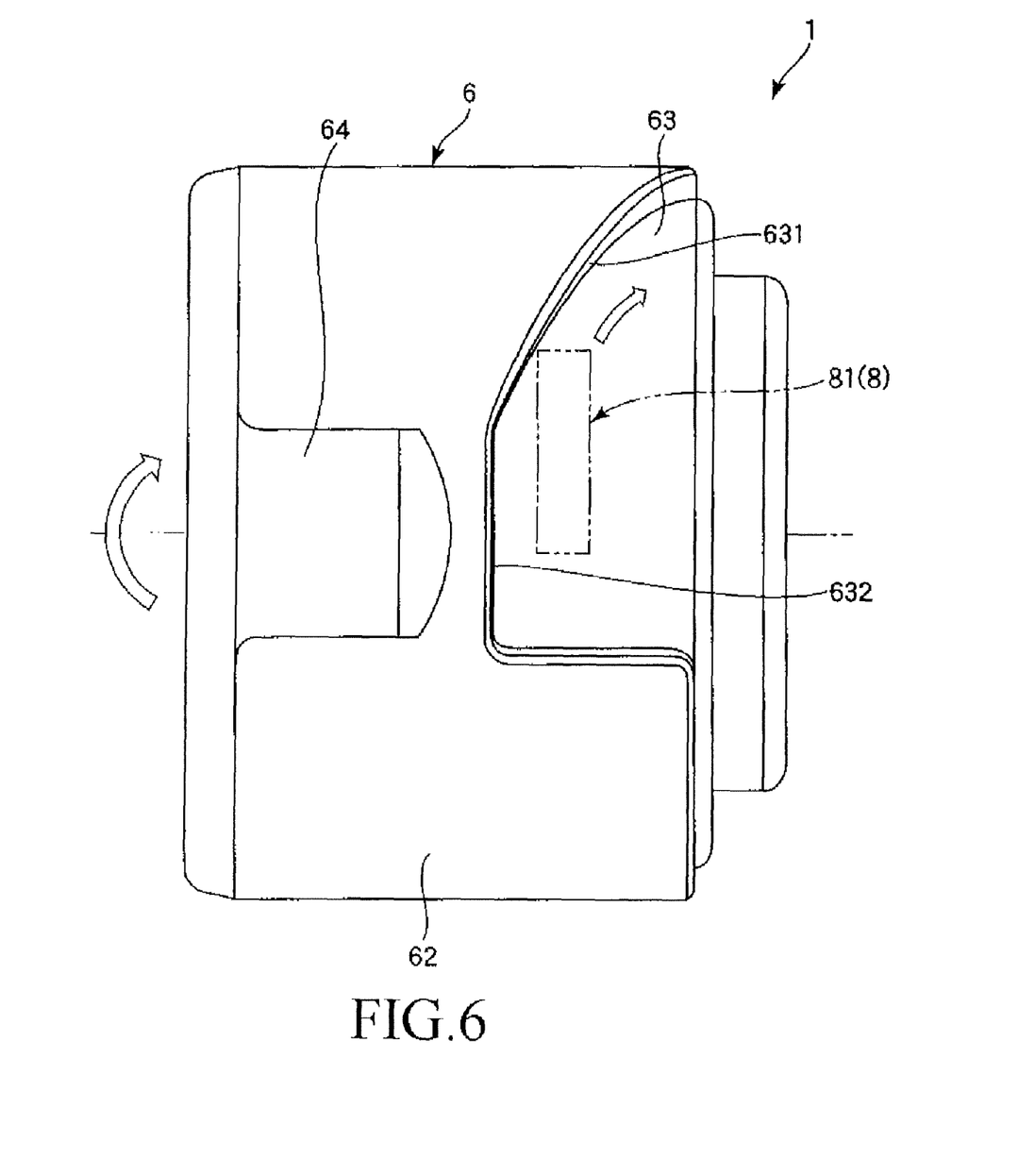
FIG. 6 is a view showing the positional relationship between the lock adapter of the syringe outer tube and the mounting section of the cap, as viewed from the direction of arrow B in FIG. 4.

FIG. 1 is a side view showing an embodiment of the syringe according to the present invention; FIG. 2 is an exploded perspective view of a distal-end side part of the syringe shown in FIG. 1; FIGS. 3 and 4 are longitudinal sectional views for sequentially showing the process of an unsealing operation of the syringe shown in FIG. 1; FIG. 5 is a view showing the positional relationship between a lock adapter of a syringe outer tube and a mounting section of a cap, as viewed from the direction of arrow A in FIG. 3; and FIG. 6 is a view showing the positional relationship between the lock adapter of the syringe outer tube and the mounting section of the cap, as viewed from the direction of arrow B in FIG. 4. Incidentally, in the following, for convenience of description, the right side in FIG. 1 and FIGS. 3 to 6 will be referred to as a "proximal end," the left side as a "distal end," the right upper side in FIG. 2 as a "proximal end," and the left lower side as a "distal end."

A syringe 1 shown in FIG. 1 is a prefilled syringe, which includes a syringe outer tube (hereafter referred to simply as "outer tube") 2, a gasket 3 disposed inside the outer tube 2 so as to be slidable along the longitudinal direction of the outer tube 2, a plunger 4 for operating to move the gasket 3, and a cap 5 mounted onto a distal end portion of the outer tube 2. A space 24 surrounded by the outer tube 2 and the gasket 3 is prefilled with a liquid such as a liquid product 200.

The outer tube 2 has an outer tube main body 21 having a tubular shape, and a lock adapter 6 as a lock member disposed at a distal end portion of the outer tube main body 21.

The outer tube main body 21 is formed at its distal end portion with a reduced diameter section 22 which is reduced in outside diameter and inside diameter. The liquid product 200 passes through the reduced diameter section 22, to be discharged via a distal end opening 221 of the reduced diameter section 22. In the outer tube 2, the reduced diameter section 22 and the lock adapter 6, by which a mating member connected to the reduced diameter section 22 is locked, constitute a spout 20 of the outer tube 2. Incidentally, the lock adapter 6 will be described later. Incidentally, the mating member to be connected to the reduced diameter section 22 is not specifically restricted; examples of the mating member include a connector disposed at an end or an intermediate portion of a tube, a mouth portion of an infusion bag, and a hub of an injection needle.

The gasket 3 has an elastic body having a cylindrical shape, and has projections 31 and 32 where its outer circumferential portion is enlarged in outside diameter. The projection 31 and the projection 32 are spaced from each other along the axial direction. The projections 31 and 32 slide while keeping close contact with an inner circumferential surface 211 of the outer tube main body 21, thereby securely maintaining gas-tightness (liquid-tightness) and enhancing slidability.

The plunger 4 has a long member, of which a distal end portion is in screwed engagement with the gasket 3. At the time of discharging the liquid product 200, the plunger 4 is pushed toward the distal direction, to cause the gasket 3 to push out the liquid product 200 from the reduced diameter section 22, whereby the discharge can be carried out easily.

As shown in FIGS. 2 to 4, the lock adapter 6 constituting the spout 20 of the outer tube 2 is ring-shaped, and is concentrically disposed at an outer circumferential portion of the reduced diameter section 22. The lock adapter 6 is for locking the mating member connected to the reduced diameter section 22.

In addition, the lock adapter 6 is supported to be movable with regard to the reduced diameter section 22 in the axial direction of the reduced diameter section 22, but is restricted in rotation around the axis. For example, as shown in FIGS. 3 and 4, such a support constitution may include a plurality of projections 61 formed on an inner circumferential portion of the proximal end of the lock adapter 6, and grooves (not shown) which are formed in an outer circumferential portion of the reduced diameter section 22 along the axial direction and in which the projections 61 are inserted, respectively.

At an outer circumferential portion 62 of the lock adapter 6 is provided with a pair of grooves 63 disposed with its axis therebetween (see FIGS. 3 and 4). The grooves 63 are portions in which projections 81 of a mounting section 8 of the cap 5 described later are inserted, respectively.

Incidentally, each of the grooves 63 may be formed across the whole circumference of the outer circumferential portion 62 of the lock adapter 6, but, in this embodiment, it is formed at a part in the circumferential direction of the outer circumferential portion 62 (see FIGS. 5 and 6). The grooves 63 have the same configuration; in the following, therefore, one of the grooves 63 will be described representatively.

As shown in FIG. 5 (and in FIG. 6, also), the groove 63 can be divided into an inclined section 631, and a perpendicular section 632 formed continuously with the distal end of the inclined section 631.

The inclined section 631 is a part where a side wall of the groove 63 is formed at an inclination relative to the axis of the lock adapter 6.

The perpendicular section 632 is a part where the side wall of the groove 63 is formed in a perpendicular direction relative to the axis of the lock adapter 6, that is, formed along the circumferential direction of the outer circumferential portion 62 of the lock adapter 6.

In addition, the outer circumferential portion 62 of the lock adapter 6 is formed with grooves 64 along the axial direction of the lock adapter 6, on the distal end side of the perpendicular sections 632. At the time of mounting the cap 5 onto the spout 20 of the outer tube 2, the cap 5 is pushed toward and onto the outer tube 2 from the distal end side. The projections 81 of the mounting portion 8 are first inserted into the grooves 64, and then inserted into the perpendicular sections 632 by riding over the portions between the grooves 64 and the perpendicular sections 632.

Thus, when the cap 5 is pushed toward and onto the outer tube 2, the cap 5 is easily mounted onto the lock adapter 6 (see FIG. 2). Then, in this condition, the liquid product 200 can be charged from the proximal end side of the outer tube 2.

As shown in FIG. 3 (and in FIG. 4, as well), the lock adapter 6 is formed at its inner circumferential portion with a female screw 65. When the mating member has a male screw, the female screw 65 can make screw engagement with the male screw. By this screw engagement, the outer tube 2 and the mating member are connected to each other assuredly.

Incidentally, the materials constituting the outer tube 2 and the plunger 4 are not specifically restricted. Examples of the materials include various resins such as polyethylene, polypropylene, polystyrene, polycarbonate, and cyclic polyolefin.

In addition, the material constituting the gasket 3 is not particularly limited. Examples of the material include various rubber materials (especially, vulcanized ones) such as natural rubber, isoprene rubber, butadiene rubber, styrene-butadiene rubber, butyl rubber, silicone rubber, fluororubber, and also include various thermoplastic elastomer, which may be used either singly or as a mixture of two or more of them.

As shown in FIGS. 1 and 3, when the syringe 1 is in an unused state, the cap 5 is mounted on the spout 20 of the outer tube 2 (hereafter, this state will be referred to as "mounted state"). Incidentally, in the case where the syringe 1 in this mounted state is to be used, unsealing can be effected by rotating the cap 5 (see FIG. 4).

The cap 5 includes a cap main body 7, the mounting section 8 disposed on the proximal end side of the cap main body 7, and a breaking section 9 which has the function to link the cap main body 7 and the mounting section 8 (see FIG. 3).

The cap main body 7 includes a tube body 71 having a tubular shape, and a sealing member 72 disposed inside the tube body 71.

The tube body 71 functions as a grip section which is gripped when unsealing is effected by rotating the cap 5. As shown in FIG. 2, an outer circumferential portion 711 of the tube body 71 is so shaped that the width in one of the radial directions gradually decreases toward the distal-end direction. This ensures that the tube body 71 has a flat shape, which permits easy gripping.

As shown in FIG. 3, at inner circumferential portions of the proximal end of the tube body 71, a plurality of ribs 73 are projectingly formed. Each of the ribs 73 is formed along the axial direction of the tube body 71. In addition, the ribs 73 are respectively disposed at regular equiangular intervals around the axis of the tube body 71. In the cap main body 7, the sealing member 72 is pressed into the part of the tube body 71 at which the ribs 73 are formed.

The sealing member 72 seals the distal end opening 221 of the reduced diameter section 22 constituting the spout 20, in a liquid-tight manner. The sealing member 72 has a disk-shaped elastic body. This ensures that the sealing member 72, in the state of being disposed in the tube body 71, is compressed toward the center by the ribs 73, whereby the sealing member 72 is prevented from slipping off from the tube body 71.

Incidentally, in the mounted state shown in FIG. 3, the sealing member 72 is compressed by the distal end opening 221 of the reduced diameter section 22 of the outer tube 2. This ensures that the distal end opening 221 can be assuredly sealed in a liquid-tight manner. Further, the thus compressed sealing member 72 is biasing the cap main body 7 toward the distal-end direction by its own elastic force. This biasing force, at the time of separating the cap main body 7 from the mounting section 8, assists the separation.

In the cap main body 7 constituted as above, in the mounted state, the sealing member 72 is in abutment with the distal end opening 221 of the reduced diameter section 22, so that a further movement of the cap main body 7 toward the proximal direction is restricted.

On the proximal end side of the cap main body 7, the ring-shaped mounting section 8 is disposed. The mounting section 8 is a member to be mounted onto the outer circumferential portion 62 of the lock adapter 6.

As shown in FIG. 3, the mounting section 8 is formed at its inner circumferential portion with the projections 81. Preferably, a plurality of the projections 81 are provided; in this embodiment, a pair of, or two, projections 81 are provided. These projections 81 are located opposite to each other, with the axis of the mounting section 8 therebetween. As shown in FIG. 3, in the mounted state, one of the pair of projections 81 is inserted in one of the grooves 63 of the lock adapter 6, while the other projection 81 is inserted in the other groove 63 of the lock adapter 6.

In addition, as shown in FIG. 5, in the state before the unsealing operation of the cap 5, each of the projections 81 is located at the perpendicular section 632 of the corresponding groove 63. When the unsealing operation is conducted, as shown in FIG. 6, each of the projections 81 is displaced from the perpendicular section 632 to the inclined section 631, and can be moved along the inclined section 631. This unsealing operation will be described later.

As mentioned above, in the cap 5, the pair of projections 81 are located opposite to each other, with the axis of the mounting section 8 therebetween, and the pair of grooves 63 are formed correspondingly to the pair of projections 81 located in this manner. This ensures that, at the time of rotating the cap 5 relative to the outer tube 2, the rotating operation can be carried out in a stable manner.

As shown in FIG. 3, the breaking section 9 is provided between the cap main body 7 and the mounting section 8. In the mounted state, the breaking section 9 links a proximal end 712 of the tube body 71 of the cap main body 7 and a distal end 82 of the mounting section 8. Then, the breaking section 9 is a part which can release the linkage between the cap main body 7 and the mounting section 8 by breaking when the unsealing operation is conducted, as shown in FIG. 4.

The breaking section 9 has a plurality of thin portions 91 arranged intermittently around the axis of the cap 5 (the mounting section 8). This permits the breaking section 9 to be easily broken at the time of the unsealing operation.

Incidentally, the number of the thin portions 91, which depends on the size and the material of the cap 5, is, for example, preferably two to eight, more preferably four to six.

In addition, the thickness of each of the thin portions 91, which also depends on the size and the material of the cap 5, is, for example, preferably 0.1 to 2.0 mm, more preferably 0.2 to 0.6 mm.

Incidentally, the material constituting the cap 5 (exclusive of the sealing member 72) is not particularly restricted; for example, the same material as the material constituting the outer tube 2 and the plunger 4 can be used.

In this case, at the time of manufacturing the cap 5, it is possible to integrally form the cap main body 7 (exclusive of the sealing member 72), the mounting section 8 and the breaking section 9.

In addition, the material constituting the sealing member 72 is not specifically restricted; for example, the same material as the material constituting the gasket 3 can be used.

Now, the process of unsealing by rotating the cap 5 from the mounted state will be described below referring to FIGS. 3 to 6.

As shown in FIG. 3, when the syringe 1 is in the unused state, the cap 5 is mounted on the outer tube 2 and the reduced diameter section 22 of the outer tube 2 is sealed in a liquid-tight manner.

Further, in this state, the projections 81 of the mounting section 8 of the cap 5 are located at the perpendicular sections 632 of the grooves 63, respectively (see FIG. 5).

Then, while the outer tube 2 is gripped by one hand, the cap main body 7 of the cap 5 is gripped by the other hand and is rotated around the axis of the outer tube 2. In this instance, the rotating force applied to the cap main body 7 is transmitted also to the mounting section 8 through the thin portions 91, and each of the projections 81 of the mounting section 8 is moved from the perpendicular section 632 to the inclined section 631 (see FIGS. 4 and 6). Further, when the rotating operation is continued, each of the projections 81 of the mounting section 8 is moved along the inclined section 631. By this movement, the mounting section 8 is gradually displaced in the proximal direction, and, concurrently, each of the thin portions 91 is gradually pulled in the same direction. Then, each of the thin sections 91 eventually breaks when the breaking limit thereof is exceeded (see FIG. 4). As a result, the cap main body 7 can be separated, or disengaged, from the mounting section 8, so that the syringe 1 is unsealed.

In addition, when the cap main body 7 is separated, the female screw 65 of the lock adapter 6 of the outer tube 2 protrudes (see FIG. 4). This enables the lock adapter 6 and the mating member to be put into screw engagement with each other.

Thus, in this syringe 1, the cap main body 7 and the mounting section 8 are linked to each other through the thin portions 91, so that breaking of the thin portions 91 makes it impossible for the cap main body 7 and the mounting section 8 to be re-linked to each other. This securely prevents an attempt to establish the mounted state again, or an attempt to make recapping, from being achieved successfully, so that it is possible to easily recognize that the syringe 1 has already been unsealed. Therefore, the syringe 1 is excellent in tamper-proofness (the property ensuring that the fact that the syringe 1 has once been put into the usable state can be confirmed afterward), and erroneous use of the syringe 1 which has previously been unsealed can be securely prevented from occurring.

Further, since the recapping is prevented, even when the unsealed syringe 1 is tampered with, use of the tampered syringe 1 by mistake can be assuredly prevented from occurring.

In addition, as shown in FIGS. 5 and 6, though each of the projections 81 of the mounting section 8 can be moved from the perpendicular section 632 to the inclined section 631 of the groove 63, movement in the opposite direction is restricted. This restricts the operating direction of the rotating operation, so that the rotating operation can be securely made in the correct direction, that is, the direction for unsealing.

Further, as above-mentioned, each of the grooves 63 of the lock adapter 6 of the outer tube 2 is formed at a part in the circumferential direction of the outer circumferential portion 62. Such a structure ensures that, at the time of the rotating operation, the mounting section 8 can be speedily pushed in the proximal direction to be separated from the cap main body 7, as compared with the case where, for example, each of the grooves 63 is formed over the whole circumference of the outer circumferential portion 62. Consequently, the syringe 1 is easy to unseal.

While the syringe according to the present invention has been described above with reference to the embodiment shown in the drawings, the invention is not to be restricted to this embodiment. Each of the components of the syringe can be replaced by one having arbitrary constitution that can exhibit the equivalent function. Further, arbitrary constitution may be added.

In addition, while the syringe in the present embodiment has the lock adapter, this constitution is not restrictive; for example, the lock adapter may be omitted.

Further, while the syringe in this embodiment has a constitution in which the outer tube (lock adapter) is formed with the grooves whereas the cap is formed with the projections to be inserted in the grooves, this constitution is not restrictive; for example, constitution may be adopted in which the outer tube is formed with the projections whereas the cap is provided with the grooves in which the projections are to be inserted.

INDUSTRIAL APPLICABILITY

The syringe according to the present invention is a syringe including: a syringe outer tube having a tubular shape to be filled with a liquid and provided with a spout through which the liquid passes at a distal end portion thereof; and a cap mounted to the spout. The cap includes: a cap main body which seals the spout in a liquid-tight manner; a ring-shaped mounting section which is disposed on a proximal end side of the cap main body and is mounted onto an outer circumferential portion of the spout; and a breaking section which links the cap main body and the mounting section and a link is releasable by breaking. One of an inner circumferential portion of the mounting section and the outer circumferential portion of the spout is formed with at least one projection, while the other is formed with a groove into which the projection is inserted and which has an inclined section that is inclined in relation to an axis of the other. When the cap is rotated relative to the syringe outer tube around an axis of the syringe outer tube, the projection moves along the inclined section of the groove, whereby the mounting section is displaced in a proximal direction, and the breaking section is pulled in the same direction to break, thereby separating the cap main body from the mounting section so that the cap main body thus separated from the mounting section cannot be mounted again onto the spout. Therefore, since the cap main body and the mounting section are linked to each other through the breaking section in an unused state, when the cap is rotated in order to unseal the syringe, the breaking section breaks. This makes it impossible to re-link the cap main body and the mounting section. Consequently, the spout of the syringe outer tube is securely prevented from being sealed again with the cap main body, which makes it possible to easily recognize that the syringe has already been unsealed. Thus, the syringe is excellent in tamperproofness, and the unsealed syringe is securely prevented from being used by mistake. Accordingly, the syringe of the present invention has industrial applicability.

The invention claimed is:

1. A syringe comprising:
a syringe outer tube having a tubular shape to be filled with a liquid and provided with a spout through which the liquid passes at a distal end portion thereof; and
a cap mounted to the spout,
wherein the cap includes a cap main body which seals the spout in a liquid-tight manner, a ring-shaped mounting section which is disposed on a proximal end side of the cap main body and is mounted onto an outer circumferential portion of the spout, and a breaking section which links the cap main body and the mounting section and a link is releasable by breaking,
one of an inner circumferential portion of the mounting section and the outer circumferential portion of the spout is formed with at least one projection, while the other is formed with a groove into which the projection is inserted and which has an inclined section that is inclined in relation to an axis of the other, and
when the cap is rotated relative to the syringe outer tube around an axis of the syringe outer tube, the projection moves along the inclined section of the groove, whereby the mounting section is displaced in a proximal direction relative to the spout and the cap main body, and the breaking section is pulled in the same direction to main body thus separated from the mounting section cannot be mounted again onto the spout.

2. The syringe a cording to claim 1,
wherein the projection is disposed at the inner circumferential portion of the mounting section, and
the groove is disposed at the outer circumferential portion of the spout.

3. The syringe according to claim 2,
wherein the spout includes:
a reduced diameter section having a reduced outside diameter; and
a ring-shaped lock adapter which is concentrically disposed at an outer circumferential portion of the reduced diameter section and which locks a mating member connected to the reduced diameter section, the groove is disposed at an outer circumferential portion of the lock adapter.

4. The syringe according to claim 1, wherein a plurality of the projections are disposed, and the groove is disposed correspondingly to each of the projections respectively.

5. The syringe according to claim 1, wherein the distal end portion of the spout includes a distal end opening through which the liquid passes, and further comprising a sealing member in the cap main body at a position spaced from the breaking section, the distal end portion of the spout contacting the sealing member so that the sealing member closes the distal end opening in a liquid-tight manner.

6. A syringe comprising:

a syringe outer tube possessing a tubular shape to be filled with a liquid and provided with a spout through which the liquid passes at a distal end portion of the spout; and a cap mounted to the spout, wherein the cap includes a cap main body which seals the spout in a liquid-tight manner, a ring-shaped mounting section which is disposed on a proximal end side of the cap main body and is mounted onto an outer circumferential portion of the spout, and a breakable breaking section serving as a link which links the cap main body and the mounting section so that rotation of the cap main body relative to the spout is transmitted to the mounting section by way of the breaking section such that the ca p main body and the mounting section rotate together until the breaking section breaks and thus releases the link between the cap main body and the mounting section, one of an inner circumferential portion of the mounting section and the outer circumferential portion of the spout includes at least one projection, while the other includes a groove in which the projection is positioned and which has an inclined section that is inclined in relation to an axis of the other, and when the cap is rotated relative to the syringe outer tube around an axis of the syringe outer tube while the breaking section links the cap main body and the mounting section, the mounting tube rotates and so the projection moves along the inclined section of the groove to cause the mounting section to move in a direction away from the cap main body and in a proximal direction relative to the spout such that the breaking section is pulled to break the link between the cap main body and the mounting section, thereby separating the cap main body from the mounting section so that the cap main body thus separated fro n the mounting section cannot be mounted again onto the spout.

7. The syringe according to claim 6, wherein the projection is disposed at the inner circumferential portion of the mounting section, and the groove is disposed at the outer circumferential portion of the spout.

8. The syringe according to claim 7, wherein the spout includes:

a reduced diameter section having a reduced outside diameter; and a ring-shaped lock adapter which is concentrically disposed at an outer circumferential portion of the reduced diameter section and which locks a mating member connected to the reduced diameter section, the groove is disposed at an outer circumferential portion of the lock adapter

9. The syringe according to claim 6, wherein the at least one projection includes a plurality of the projections, and the groove is disposed

10. The syringe according to claim 6, wherein the distal end portion of the spout includes a distal end opening through which the liquid passes, and further comprising a sealing member in the cap main body at a position spaced from the breaking section, the distal end portion of he spout contacting the sealing member so that the sealing member closes the distal end opening in a liquid-tight manner.

\* \* \* \* \*